United States Patent [19]
Stein et al.

[11] Patent Number: 5,929,348
[45] Date of Patent: Jul. 27, 1999

[54] MICRO SLED IMPACT TEST DEVICE

[75] Inventors: Douglas J. Stein, Oxford; Frederick M. Peters, St. Clair, both of Mich.

[73] Assignee: Autoliv ASP, Inc., Ogden, Utah

[21] Appl. No.: 09/010,029

[22] Filed: Jan. 21, 1998

[51] Int. Cl.$^6$ .................................................. G01M 19/00
[52] U.S. Cl. .......................................... 73/865.3; 73/12.07
[58] Field of Search ................................ 73/865.3, 865.9, 73/12.07, 12.04, 866.5

[56] References Cited

U.S. PATENT DOCUMENTS

| | | | |
|---|---|---|---|
| 5,483,845 | 1/1996 | Stein et al. | 73/865.3 |
| 5,485,758 | 1/1996 | Brown et al. | 73/865.8 |
| 5,623,094 | 4/1997 | Song et al. | 73/12.07 |

*Primary Examiner*—Hezron Williams
*Assistant Examiner*—Thuy Vinh Tran
*Attorney, Agent, or Firm*—Ohlandt, Greeley, Ruggiero & Perle, L.L.P.; George W. Rauchfuss, Jr.

[57] ABSTRACT

An apparatus for dynamic testing by rapidly accelerating a test specimen includes a sled carriage slidably mounted on first and second elevated horizontal tracks attached to a fixed foundation for free movement of the sled carriage along the tracks from a first to a second track location; the sled carriage having an essentially horizontal mounting plate terminating in a leading edge at one end and a trailing edge at an opposite end; and impact block mounted to the bottom surface of the mounting place intermediate the leading and trailing edges; a pressure differential firing component having a moveable thrust surface for striking the impact block; the pressure differential firing component attached to the foundation between the tracks so at least a portion of the bottom surface of the mounting plate of the sled carriage between the leading edge and the impact block can override at least a portion of a firing chamber component of the pressure differential firing component; a high pressure compressed gas storage chamber attached to the foundation between the tracks in a position substantially parallel to the firing chamber; and manifold component fluidly connecting the gas storage chamber with the firing chamber whereby, upon actuation of a trigger component, gas in the gas chamber causes the thrust surface to strike the impact block whereby longitudinal movement is imparted to the sled carriage to cause propelled movement of the sled carriage from the first to the second track location.

14 Claims, 5 Drawing Sheets

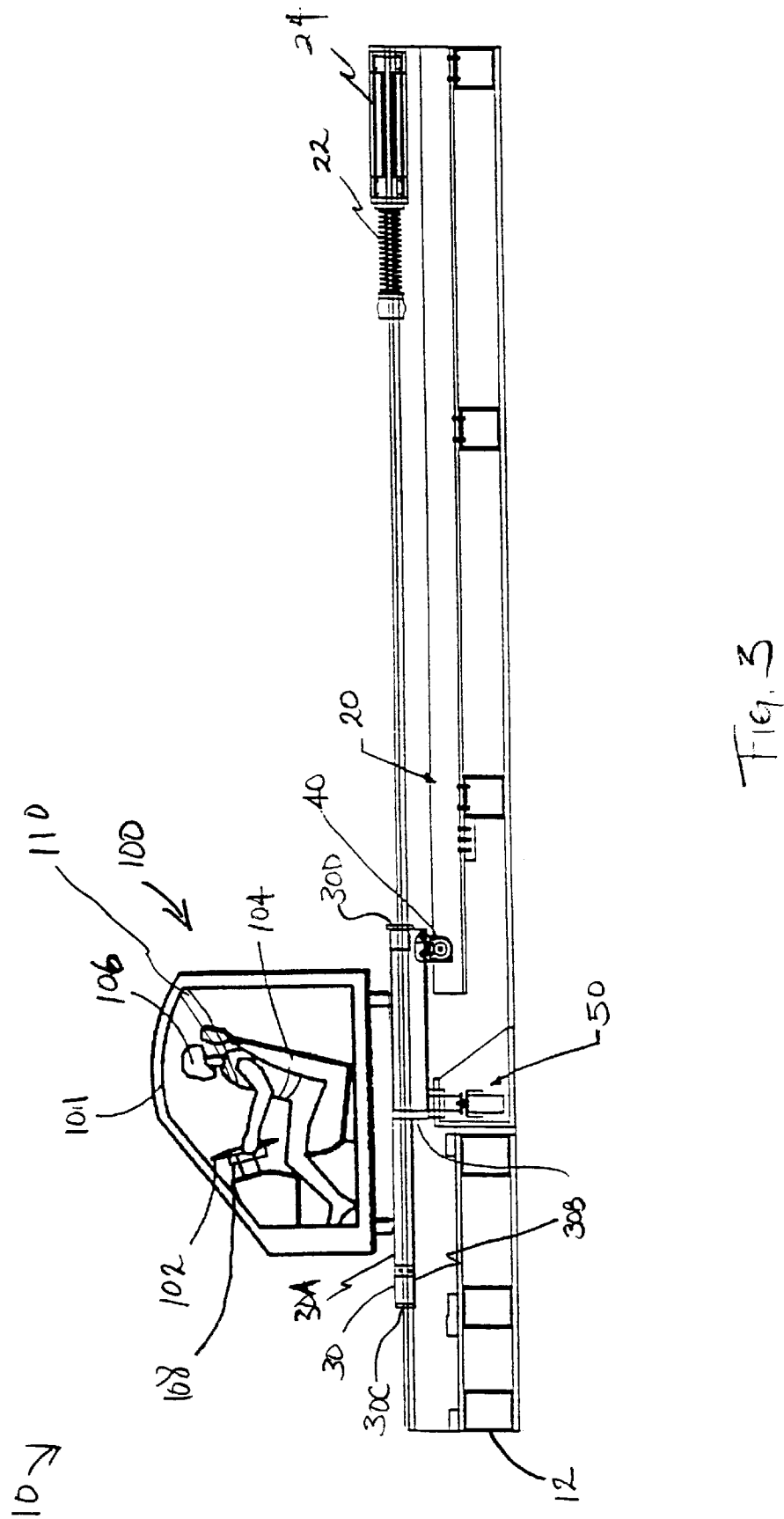

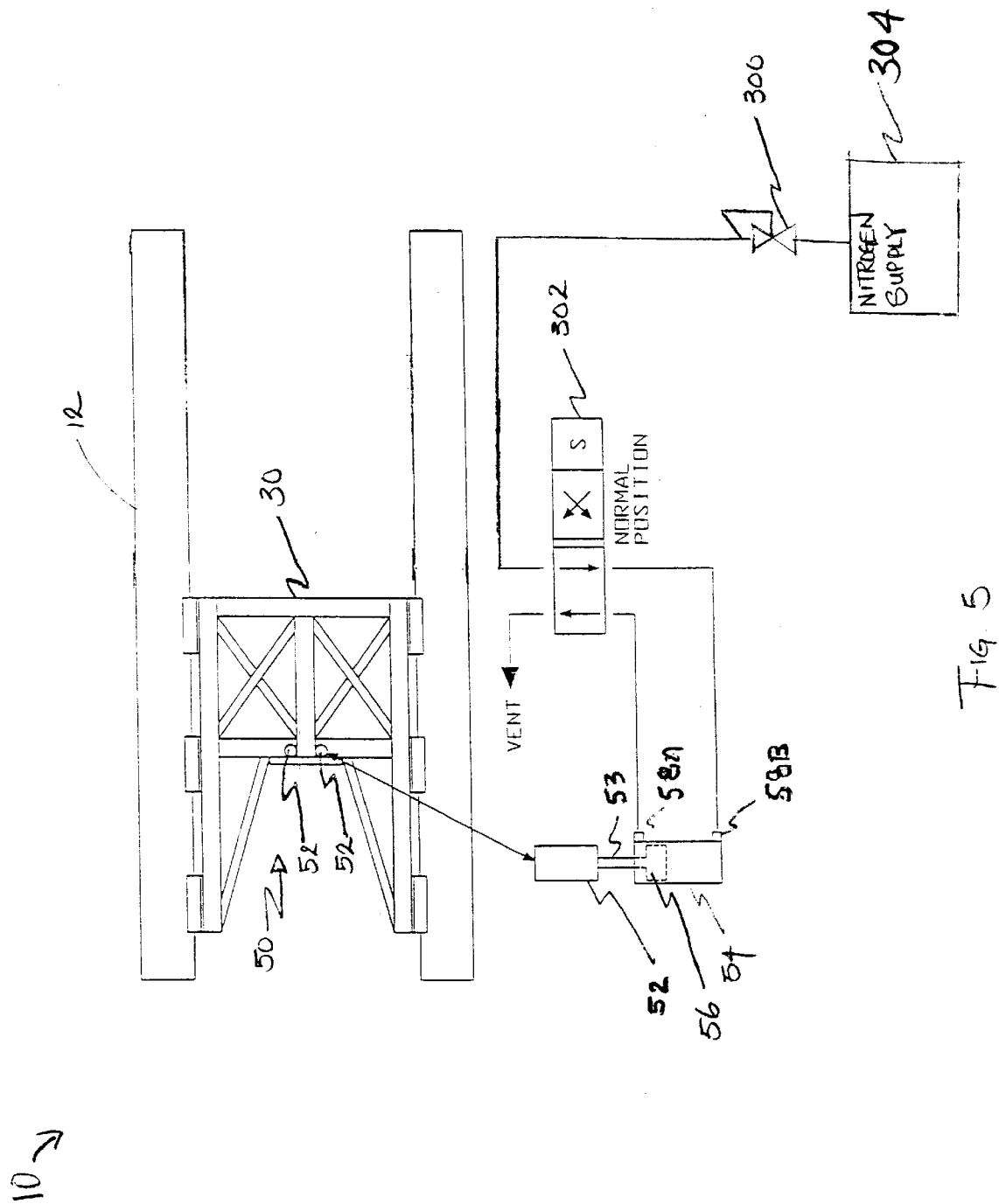

MICRO SLED IMPACT TEST DEVICE

FIELD OF THE INVENTION

The present invention relates to an apparatus for impact testing and, more particularly, for impact testing in simulated automobile crashes and dynamic testing of passenger restraint devices, such as seat belts and airbags.

BACKGROUND OF THE INVENTION

There is currently various devices and methods for testing passenger restraint devices, such as airbags and seat belts. For instance, full size automobiles are sometimes employed by the government and automotive industry for final impact testing. However, it is generally impractical to use full size automobiles for impact testing, particularly during design and research stages necessary to ensure compliance with government mandated safety standards.

Another type of impact testing method and device, typically referred as HYGE crash simulator, is currently employed to simulate crash conditions, an example of which is described in U.S. Pat. No. 5,483,845 to Stein et al. Such devices typically include a pressure differential firing means, utilizing both hydraulic and pneumatic pressures, which terminates in a thrust column. Upon actuation of the firing means, the thrust column accelerates a sled carriage suitably mounted on a track to be movable along the track. A test buck housing a forward facing vehicle occupant or driver specimen, generally in the form of an anthropomorphic dummy, is fixedly mounted on the sled carriage. Acceleration of the sled carriage by the thrust column produces rapid acceleration of the movable sled carriage and thereby also the test buck. As a result of the rapid acceleration of the sled carriage and test buck along the track, the occupant or driver test specimen is subjected to a rapid change in longitudinal velocity relative to the test buck, thereby simulating an impact crash of an automobile vehicle.

The problem with such impact testing devices is that they are too large, typically requiring a minimum room size of about 20 feet wide×100 feet long×12 feet high. Such testing devices are also very expensive (i.e., typically sold for $1,200,000) and require an enormous amount of foundation network and preparation prior to installation. Such problems are associated in part to the arrangement of the firing means which typically has both the pneumatic and hydraulic cylinders arranged along a longitudinal axis, thereby requiring a significant amount of room to be allocated thereto. The sled carriage and tracks are also arranged at a distance from each other with the firing means adapted to strike a front end of the sled carriage. Such an arrangement also increases the overall length of the impact testing device.

There is a need for a compact, inexpensive impact testing device for conducting performance comparison and evaluation tests on passenger restraint devices, such as airbag and set belt systems, prior to testing these components on a HYGE crash simulator. There is also a need for a test device which enables such tests to be performed efficiently and quickly to reduce new module development time.

SUMMARY OF THE INVENTION

Accordingly, it is an object of the present invention to provide an inexpensive, compact testing device for conducting performance comparison and evaluation tests on airbag and seat belt systems prior to testing these components on a HYGE crash simulator.

It is a further object of the invention to provide a testing device that enables tests to be performed efficiently and quickly to reduce new module development time.

Another object of the invention is to provide an impact testing device that employs a compact thrust apparatus to accelerate a sled carriage.

In view of the foregoing, the present invention is an apparatus for dynamic testing by rapidly accelerating a test specimen. The present apparatus includes (1) a sled carriage slidably mounted on opposing, essentially parallel first and second elevated horizontal tracks attached to a fixed foundation for free longitudinal movement of the sled carriage along the first and second tracks from a first location to a second location on the tracks, the sled carriage having an essentially horizontal mounting plate having top and bottom surfaces terminating in a leading edge at one end and a trailing edge at an opposite end of the mounting plate; (2) impact block mounted to the bottom surface of the mounting place intermediate the leading and trailing edges; (3) a pressure differential firing component comprising trigger component and a firing chamber component having a moveable thrust surface for striking the impact block, the pressure differential firing component attached to the fixed foundation between the elevated horizontal first and second tracks so at least a portion of the bottom surface of the mounting plate of the sled carriage between the leading edge and the impact block can override at least a portion of the firing chamber component of the pressure differential firing component; a high pressure compressed gas storage chamber attached to the fixed foundation between the elevated horizontal first and second tracks in a position substantially parallel to the firing chamber of the pressure differential firing chamber; and (4) manifold component fluidly connecting the high pressure compressed gas storage chamber with the pressure differential firing chamber whereby, upon actuation of the trigger component, high pressure gas in the compressed gas chamber causes the thrust surface to strike the impact block whereby longitudinal movement is imparted to the sled carriage to cause propelled movement of the sled carriage from the first location to the second location.

The testing apparatus can be contained on a single structure of welded construction. For instance, the structure is bolted to a steel plate weighing about 13,000 pounds in order to provide increased reaction mass to the impulse of the sled propulsion event. The steel plate is then secured to the standard building floor using commercially available concrete anchors and grout. The micro sled impact testing apparatus requires only several weeks of foundation rework and construction of reinforced concrete reaction masses before the apparatus can be installed. Accordingly, such an apparatus provides a low cost impact testing system that is easier to install and requires minimal space and foundation work to install.

To accommodate the pressure differential cylinder requirements of the firing means (also referred to as "the thrust apparatus") and retain the compact design feature, the cylinder is designed in a novel manner. The half of the cylinder acting as an accumulator is positioned along side or adjacent the main cylinder portion which includes a piston and thrust column. The two halves of the cylinder are connected by a manifold to allow the compressed air to flow from the accumulator side to the cylinder side. Such an arrangement provides a compact thrust apparatus that is capable of accelerating the sled carriage to a desired velocity.

The present invention also provides a thrust apparatus and sled carriage arrangement to reduce the stack up dimensions (i.e., the height) of the testing apparatus. Instead of having the thrust column of the firing cylinder pushing on the front end of the carriage, the thrust apparatus pushes on a structure protruding from the bottom surface of the carriage near the sled carriage's longitudinal center, referred as an impact area or impact block. This design feature allows the front half of the sled carriage to ride over at least a portion of the thrust apparatus, particularly prior to initiating a test sequence.

As the overall length of the testing apparatus is much smaller than conventional test devices, the stopping distance for the sled carriage is also much shorter, approximately 10 feet as compared to 50 feet. This presents a challenge to safely stop the sled carriage in a short distance without damaging the test dummies used to measure occupant injury or the test apparatus itself. Therefore, the present invention also includes a braking system incorporated into the sled carriage, preferably a caliper brake adapted to engage a brake rail running along a longitudinal movement pathway of the sled carriage. During a braking operation, the caliper brake frictionally engages the brake rail to prevent further longitudinal movement of the sled carriage. In addition thereto, the present invention employs a set of shock absorbers mounted to an end of the carriage rails or tracks. The shock absorbers are employed in the event of extreme test conditions or brake system malfunction.

The invention together with further objects, features, advantages and aspects thereof, will be more clearly understood from the following description taken in connection with the accompanying drawings.

BRIEF DESCRIPTION OF THE DRAWINGS

FIG. 3 is a cross-sectional view of the micro sled impact device taken along the line 3—3 of FIG. 1.

The same reference numerals refer to the same elements throughout the various figures.

DETAILED DESCRIPTION OF THE INVENTION

Figure 1:
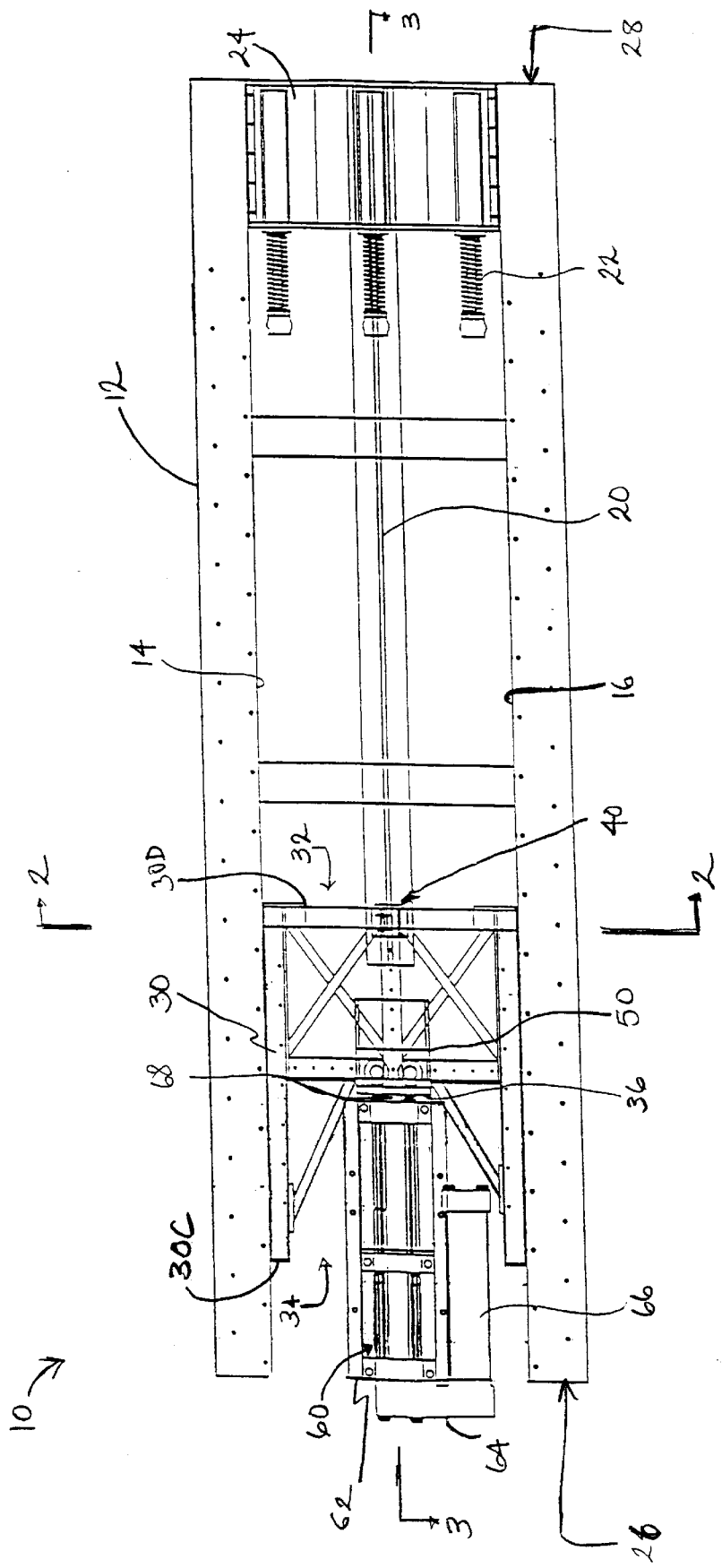
FIG. 1 is an overall view of a micro sled impact device, in accordance with the present invention.

FIG. 1 discloses a micro sled impact device 10 for dynamically testing passenger restraint devices, such as seat belts and airbags. Micro sled impact device 10 includes a base frame 12 mountable to a foundation, such as a cement floor. Base frame 12 includes an elevated first horizontal track 14 extending along at least a portion of base frame 12 between a first end 26 and a second end 28 of base frame 12, and a second elevated horizontal track 16, opposite the first track, also extending along at least a portion of base frame 12 between first and second ends 26, 28. A sled carriage 30 is mounted on tracks 14, 16 of base frame 12 in a manner to be slidably movable in a longitudinal direction along tracks 14, 16. Sled carriage 30 includes a bottom surface 30B having extending therefrom an impact area o:r block 36, and a top surface 30A for mounting a device and components to be tested (FIGS. 2 and 3).

A compact pressure differential thrust apparatus 60 for accelerating sled carriage 30 is mounted to base frame 12 between first and second tracks 14, 16 so at least a portion of bottom surface 30B of the mounting plate of sled carriage 30 between a leading edge 30C and impact block 36 can override at least a portion of thrust apparatus 60. Thrust apparatus 60 includes a firing chamber 62 having a movable thrust column 68 for striking impact block 36; and an accumulator 66 for storing high pressure compressed gas attached to base frame 12 between first and second tracks 14, 16 in a position substantially parallel to firing chamber 62. A manifold means 64 fluidly connects accumulator 66 with firing chamber 62. Upon actuation of a trigger means (not shown), high pressure gas in firing chamber 62 causes thrust column 68 to accelerate to a velocity required to replicate crash parameters and to strike impact block 36 whereby longitudinal movement is imparted to sled carriage 30 to cause propelled movement of sled carriage 30 from a first location, i.e., from a position at or near first end 26 to a second location, i.e., to a position at or near second end 28. It has been discovered that thrust apparatus 60, as described above, provides a compact firing mechanism for accelerating sled carriage 30, thereby reducing the overall dimensions and costs of micro sled impact device 10.

Figure 2:
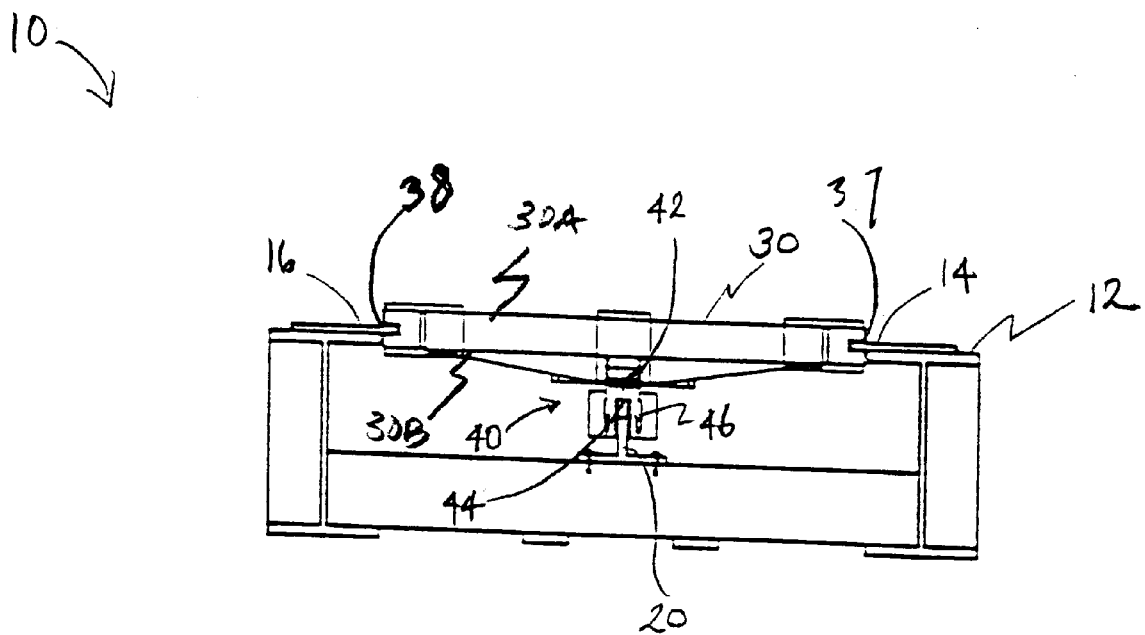
FIG. 2 is a side view of the micro sled impact device of FIG. 1.

FIG. 2 is a cross-sectional view of micro sled impact device 10. As shown, sled carriage 30 includes a first channel 37 on an edge between leading edge 30C and trailing edge 30D of sled carriage 30 and a second channel 38 on an opposite edge of the first channel. Both first and second channels 37, 38 are slidably mounted to first track 14 and second track 16 of base frame 12, respectively. Although the above describes a preferred arrangement for slidably mounting sled carriage 30, it should be understood that sled carriage 30 may be slidably mounted in any manner so as to move from the first position to the second position, upon impact of thrust column 68 on impact block 36. For example, sled carriage 30 may be arranged with tracks and base frame 12 may be arranged with corresponding channels, sled carriage 30 may include wheels, and so forth.

Referring to FIGS. 2 and 3, there is shown a braking system 40, incorporated in sled carriage 30, for preventing further longitudinal motion of sled carriage 30. Braking system 40 is preferably a caliper brake generally denoted by the reference numeral 42. Caliper brake 42 extends from a bottom surface 30B of sled carriage 30 and is positioned preferably proximal a back end 32 or trailing edge 30D of the sled carriage. Caliper brake 42 includes a base portion 44 having a pair of arms 46 extending therefrom towards a brake rail 20 that extends longitudinally along preferably a center of base frame 12. In the preferred embodiment, caliper brake 42 is adapted to move in a vertical direction (i.e., towards and away from brake rail 20) so that base portion 44 and/or arms 46 frictionally engage brake rail 20 to decelerate sled carriage 30 and to prevent further longitudinal movement of sled carriage 30 along tracks 14, 16. Caliper brake 42 can also be arranged with movable arms 46 which are positioned on opposite sides of brake rail 20 and clamp down on brake rail 20, during a braking operation. Caliper brake 42 may be automatically controlled by known methods which will not be described in detail herein.

In addition, micro sled impact device 10 further includes at least one shock absorber 22 (FIGS. 1 and 2) mounted on a foundation or an impact block 24 of base frame 12 at an end of tracks 14, 16 and proximal second end 28 of base frame 12. Shock absorbers 22 also prevents further longitudinal movement of sled carriage 30 along tracks 14, 16 and are employed in the event of brake system failure or extreme crash conditions.

Although the preferred braking system is described above, micro sled impact device 10 may include other braking systems to prevent further movement of sled carriage 30.

As shown in FIG. 3, fixedly mounted on the horizontal upper or top surface 30A of sled carriage 30 is a test buck 100 representative of the driver/front seat passenger area of a vehicle, such as an automobile or truck. Test buck 100 includes a frame structure 101, housing therein an anthropomorphic test specimen or dummy 106 suitably seated in a vehicle seat 104. As shown, test specimen 106 is seated in a typical manner adjacent to a steering wheel and column 102 housing an air bag module 108. Airbag module 108 is caused to be inflated and deployed upon actuation of a sensor, such as an accelerometer, which measures the rate of acceleration of test buck 100 and causes deployment of airbag module 108 when impact crash conditions are sensed. Test buck 100 and its component parts, namely frame structure 101, seat 104 and test specimen 106, remain stationary until thrust column 68 of thrust apparatus 60 impacts impact block 36. Although the above describes an airbag module for a front end crash, test buck 100 may also be employed to test side impact crashes, side impact airbag modules, a seat belt system 110 and other passenger restraint systems, all of which can be installed in test buck 100 and tested.

Figure 4A:
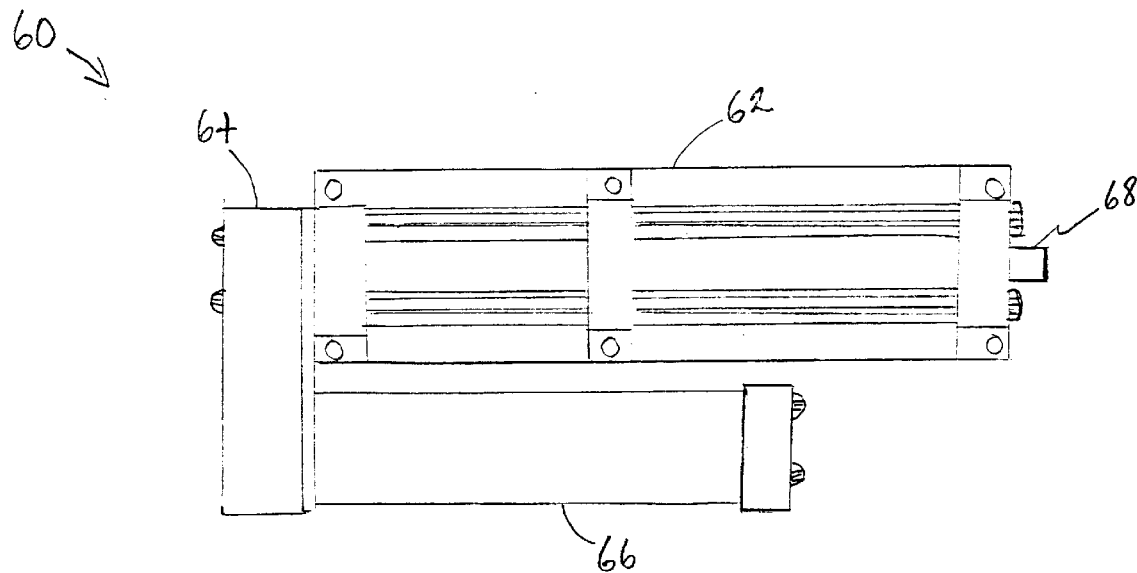
FIGS. 4A and 4B illustrate a thrust apparatus of the micro sled impact device of the present invention.
Figure 4B:
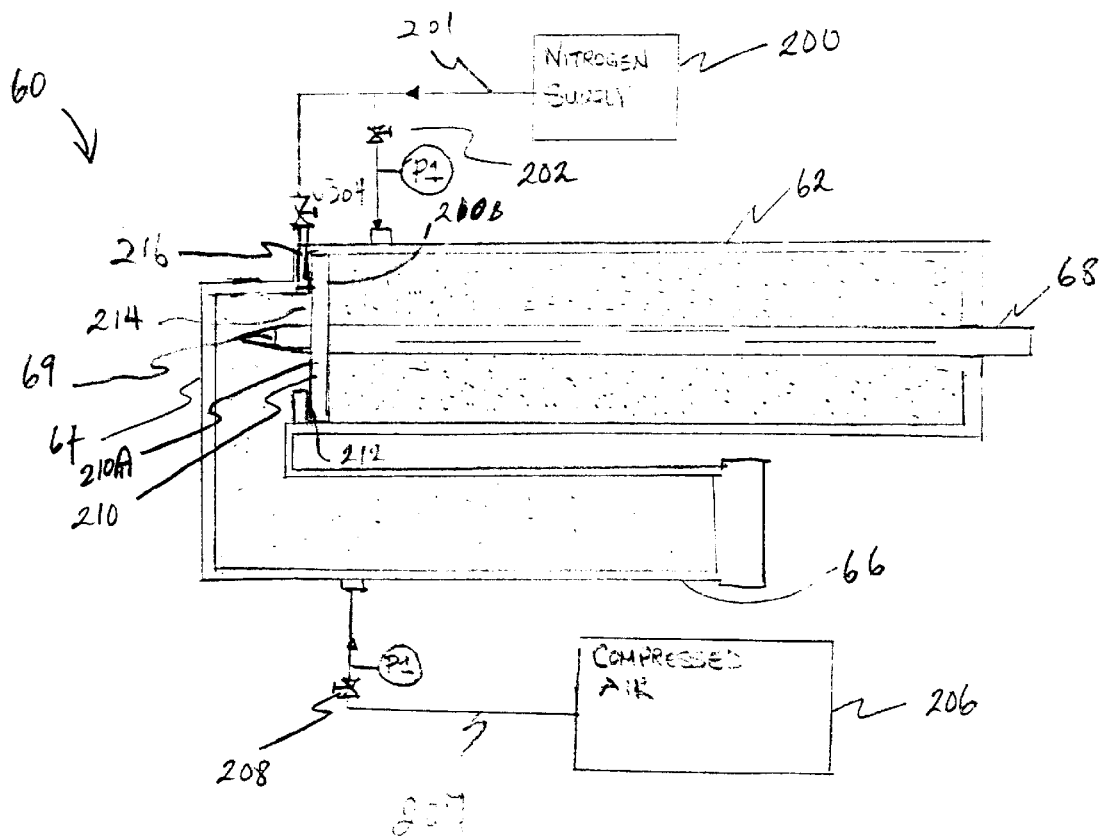
Figure 2:
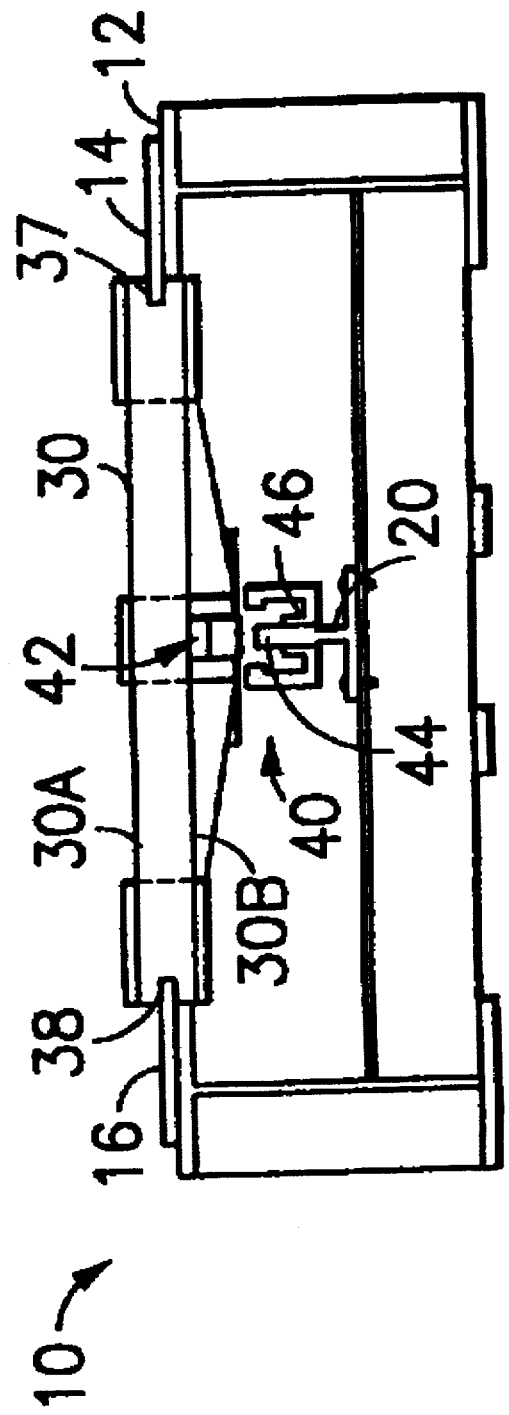
Figure 4A:
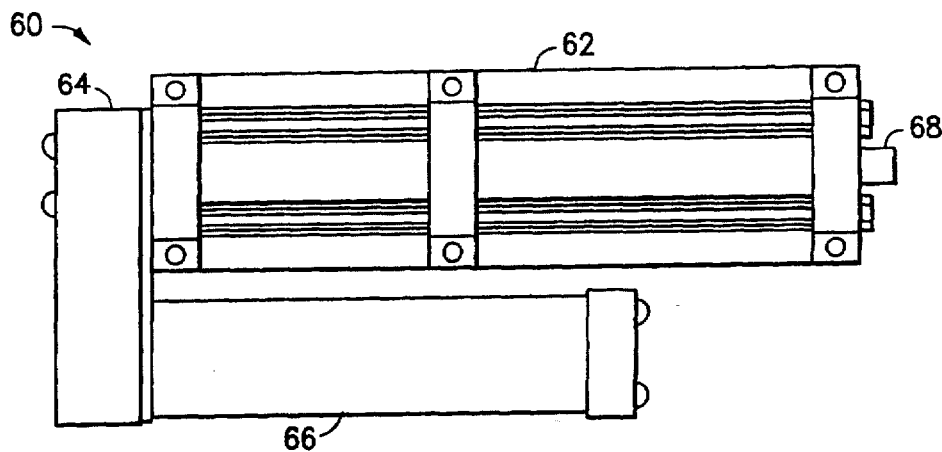
Figure 4B:
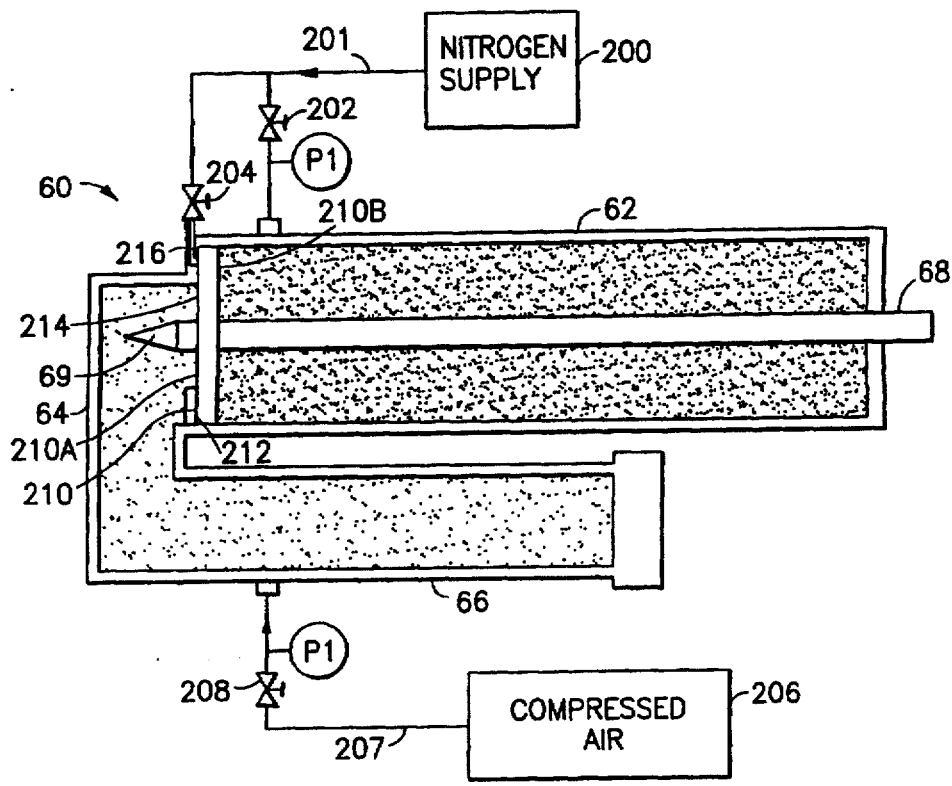

Referring to FIGS. 4A and 4B, there is shown a preferred embodiment of pressure differential thrust apparatus 60 to accelerate sled carriage 30 and components thereon from a first position at or near first end 26 to a second position at or near second end 28 to simulate crash conditions. Thrust apparatus 60 includes a thrust column 68 housed therein and is adapted to fire and rapidly accelerate thrust column 68 to a velocity required to replicate impact crash parameters. Thrust column 68 extends into firing chamber 62 and preferably has a radial thrust piston 210 located at its internal end. Thrust piston 210 is located in thrust apparatus 60 between firing chamber 62 containing low pressure compressed gas (e.g., nitrogen) and accumulator 66 and manifold 64 containing high pressure compressed gas (e.g., compressed air). As shown, firing chamber 62 and accumulator chamber 66, positioned adjacent to firing chamber 62, are fluidly connected by manifold 64. It is preferred that firing chamber 62 and accumulator 66 are positioned substantially parallel to each other. Such an arrangement provides a compact thrust apparatus which reduces the overall size (i.e., length, width and height) of the impact device of the present invention.

Firing chamber 62, and manifold 64 and accumulator chamber 66 are separated by apertured wall 212. Wall 212 serves to separate firing chamber 62 from manifold 64 and accumulator chamber 66 prior to firing by having thrust piston 210 sealed thereagainst. Aperture or orifice 214 in wall 212 serves as a metering orifice by accepting a metering pin 69 located on an internal end of thrust column 68 adjacent thrust piston 210. Thrust apparatus 60 is provided with a trigger pressure inlet 216 of highly pressurized air for initial movement of thrust piston 210, moving metering pin 69 to begin metered gas flow from accumulator chamber 66 and manifold 64 to piston 210, accelerating thrust column 68 in the manner described hereinafter. Valve 204 in inlet 216 is utilized for actuation of the firing sequence.

Prior to firing, thrust piston 210 is in sealing engagement with wall 212 due to balanced pressure on opposite sides 210A and 210B of thrust piston exposed to the high pressure chambers 64 and 66 and low pressure chamber 62. By opening valve 204 of trigger pressure inlet 216, the balanced pressure on side 210B of thrust piston 210 is disturbed and the increased pressure on side 210A of thrust piston 210 facing chambers 64 and 66 due to high pressurized air entering from inlet 216 causes thrust piston 210 to move longitudinally away from wall 212 and the resulting action of high pressure gas from chambers 64 and 66 upon the increased exposed area of the side 210A of thrust piston 210 causes rapid longitudinal acceleration of thrust column 68 for accelerating sled carriage 30 on tracks 14, 16.

Metering pin 69 of micro sled impact device 10 can be of any suitable shape. The shape is selected to provide a simulated velocity versus time profile pattern as close as possible to the pattern resulting from an actual vehicle crash desired to be simulated. It will be appreciated that the shape and length of such a metering pin 69 will vary with the structural features of various vehicles and thus one must choose a metering pin suitable for the actual vehicle being simulated.

High pressure gas chambers, namely manifold 64 and accumulator chamber 66, are filled with pressurized air from supply tank 206 via line 207 and valve 208. Similarly, low pressure chamber, namely firing chamber 62, is filled preferably with nitrogen gas from nitrogen supply tank 200 via line 201 and valve 202. Prior to firing, firing chamber 62, manifold 64 and accumulator chamber 66 are maintained at the same pressure generally indicated by the reference numeral P1 using pressure regulators.

Figure 5:
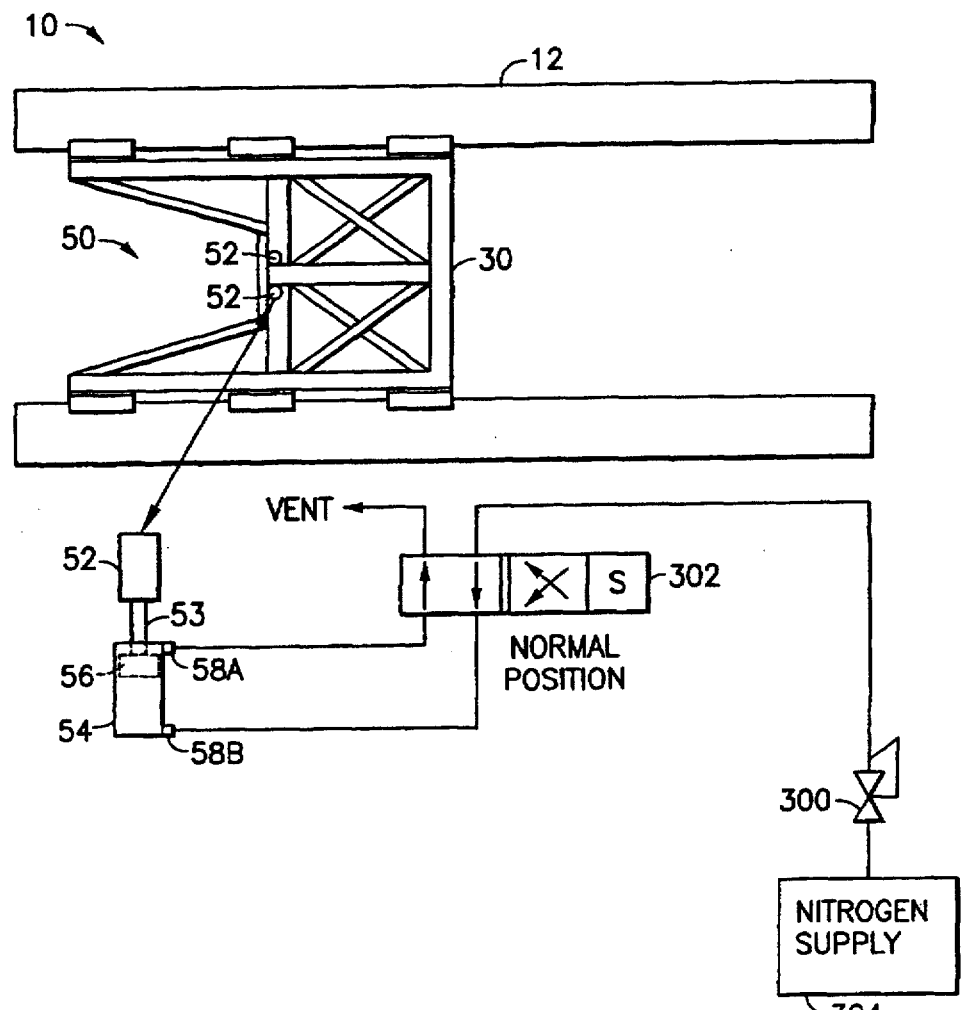
FIG. 5 illustrates a safety lock mechanism for a sled carriage of the present invention.

FIG. 5 illustrates a safety lock mechanism 50 incorporated into sled carriage 30 to prevent unwanted longitudinal movement of sled carriage 30, prior to a test operation. Safety lock mechanism 50 includes at least one carriage lock pin 52, but preferably two carriage lock pins 52, adapted to engage sled carriage 30 from bottom surface 30B to prevent movement thereof. Each carriage lock pin 52 has extending therefrom a shaft 53 having a portion thereof housed in a pressure chamber 54 having a gas inlet 58B and a vent outlet 58A. An internal end of shaft 53 is connected to a piston 56 located insider pressure chamber 54. Pressure chamber 54 is preferably filled with nitrogen gas from a gas supply 304 fluidly connected to inlet 58B. Gas supply 302 may be gas supply 200 (FIG. 4B) or a different gas supply unit. A pressure regulator 300 maintains the gas pressure of pressure chamber 54 preferably at 300 psi. The pressure from the gas causes piston 56 to be pushed upwardly towards sled carriage 30 with each pin 52 being engaged to corresponding openings (not shown) of sled carriage 30 to prevent unwanted movement of the sled carriage. The gas in pressure chamber 58 can be released, via vent outlet 58A to disengage each pin 52 from sled carriage 30. A valve 302 is employed to control the inflow and outflow of gases (via inlet 58B and outlet 58A) from pressure chamber 54.

An operational example of micro sled impact device 10 is provided below with reference with FIGS. 3, 4A and 4B. Initially, sled carriage 30 (and components mounted thereon) is positioned at or proximal first end 26 of base frame 12 so that sled carriage 30 is positioned over at least a portion of thrust apparatus 60. Pins 52 of safety lock mechanism 50 are also engaged to sled carriage 30 to prevent unwanted movement thereof, prior to testing. Upon actuation of thrust apparatus 60 (via trigger inlet 216), pins 52 are disengaged from sled carriage 30 and thrust column 68 is accelerated towards impact block 36. The accelerated thrust column 68 strikes impact block 36 of sled carriage 30, thereby rapidly accelerating sled carriage 30 and the components mounted thereon (such as dummy, passenger restraint devices, etc.) in a longitudinal direction from first end 26 of base frame 12 to second end 28 of base frame 12 at a desired velocity. As a result of the acceleration of sled carriage 30 along tracks 14, 16, the occupant and test specimen 106 and passenger restraint devices to be tested are subjected to a rapid change in longitudinal velocity to simulate crash conditions. Accordingly, passenger restraint devices, such as airbag 108 and seat belt system 110, can be tested on test specimen 106 at predetermined crash conditions.

As sled carriage 30 approaches second end 28, brake system 40 of sled carriage 30 is activated, thereby causing caliper 42 to engage frictionally brake rail 20 and decelerate the sled carriage. In the event of brake system failure or extreme test conditions, sled carriage 30 is stopped by shock absorber(s) 22 mounted on a foundation or impact block 24 of base frame 12, at or proximal to second end 28.

With the foregoing description of the invention, those skilled in the art will appreciate the modifications may be made to the invention without departing from the spirit thereof. Therefore, it is not intended that the scope of the invention be limited to the specific embodiments illustrated and described.

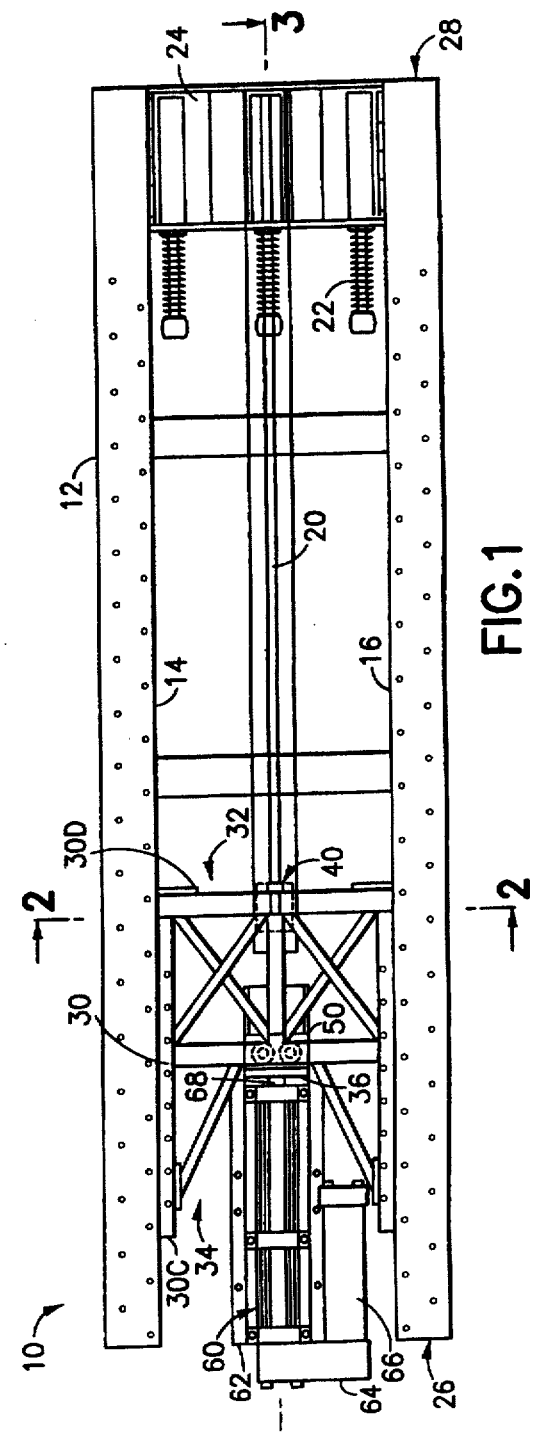

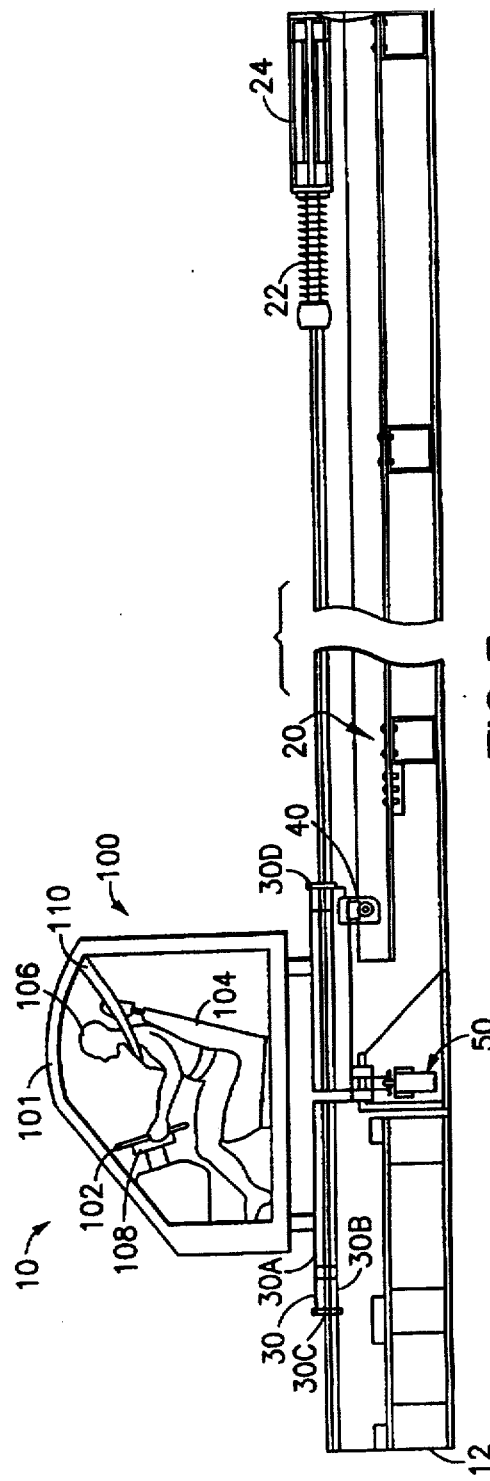

I claim:

1. Apparatus for dynamic testing by rapidly accelerating a test specimen, comprising in combination:

a sled carriage slidably mounted on opposing, essentially parallel first and second elevated horizontal tracks attached to a fixed foundation for free longitudinal movement of the sled carriage along the first and second tracks from a first location to a second location on the tracks; the sled carriage having an essentially horizontal mounting plate having top and bottom surfaces terminating in a leading edge at one end and a trailing edge at an opposite end of the mounting plate; and impact block mounted to the bottom surface of the mounting plate intermediate the leading and trailing edges;

a pressure differential firing means comprising trigger means and a firing chamber means having a moveable thrust surface for striking the impact block; the pressure differential firing means attached to the fixed foundation between the elevated horizontal first and second tracks so at least a portion of the bottom surface of the mounting plate of the sled carriage between the leading edge and the impact block can override at least a portion of the firing chamber means of the pressure differential firing means;

a high pressure compressed gas storage chamber attached to the fixed foundation between the elevated horizontal first and second tracks in a position substantially parallel to the firing chamber of the pressure differential firing chamber; and manifold means fluidly connecting the high pressure compressed gas storage chamber with the pressure differential firing chamber whereby, upon actuation of the trigger means, high pressure gas in the compressed gas chamber causes the thrust surface to strike the impact block whereby longitudinal movement is imparted to the sled carriage to cause propelled movement of the sled carriage from the first location to the second location.

2. Apparatus according to claim 1 wherein a high pressure gas chamber is attached to the fixed foundation in a position intermediate the pressure differential firing means and one of the first and second elevated horizontal tracks.

3. Apparatus according to claim 1, further comprising brake means mounted on the bottom surface of the mounting plate intermediate the impact block and the trailing edge of the mounting plate; and a brake rail mounted to the fixed foundation intermediate the first and second elevated horizontal tracks and positioned to be acted upon by the brake means to brake further longitudinal movement of the sled carriage after the propelled movement of the sled carriage from the first location to the second location.

4. Apparatus according to claim 3 further comprising one or more shock absorbers mounted directly or indirectly to the fixed foundation between the first and second elevated tracks for contacting the trailing edge of the mounting plate for stopping further propelled movement of the sled carriage.

5. Apparatus according to claim 1, further comprising a safety lock mechanism, mounted to the base frame, and having a pin adapted to move between a first position to engage the sled carriage to prevent movement thereof and a second position to disengage from the sled carriage to allow movement thereof.

6. Apparatus according to claim 1, further comprising a test buck mounted to an upper surface of the sled carriage.

7. Apparatus according to claim 6, wherein the test buck includes a frame structure member.

8. Apparatus according to claim 7, wherein the test buck further comprises seating means, mounted to one of the frame structure member or the sled carriage, for seating the test specimen.

9. Apparatus according to claim 8, wherein the test specimen is an anthropomorphic test specimen seated on the seating means.

10. Apparatus according to claim 9, wherein the test buck further includes a seat belt system to be tested for securing the test specimen to the seating means.

11. Apparatus according to claim 6, wherein the test buck further includes an airbag module to be tested.

12. A method of conducting dynamic testing by rapidly accelerating a specimen, the method comprising:

(1) providing, a sled carriage slidably mounted on opposing, essentially parallel first and second elevated horizontal tracks attached to a fixed foundation for free longitudinal movement of the sled carriage along the first and second tracks from a first location to a second location on the tracks; the sled carriage having an essentially horizontal mounting plate having top and bottom surfaces terminating in a leading edge at one end and a trailing edge at an opposite end of the mounting plate; and impact block mounted to the bottom surface of the mounting place intermediate the leading and trailing edges;

a pressure differential firing means comprising trigger means and a firing chamber means having a moveable thrust surface for striking the impact block; the pressure differential firing means attached to the fixed foundation between the elevated horizontal first and second tracks so at least a portion of the bottom surface of the mounting plate of the sled carriage between the leading edge and the impact block can override at least a portion of the firing chamber means of the pressure differential firing means;

a high pressure compressed gas storage chamber attached to the fixed foundation between the elevated horizontal first and second tracks in a position substantially parallel to the firing chamber of the pressure differential firing chamber;

manifold means fluidly connecting the high pressure compressed gas storage chamber with the pressure differential firing chamber whereby, upon actuation of the trigger means, high pressure gas in the compressed gas chamber causes the thrust surface to strike the impact block whereby longitudinal movement is imparted to the sled carriage to cause propelled movement of the sled carriage from the first location to the second location;

a test buck mounted to an upper surface of the sled carriage and housing therein a test specimen;

(2) actuating the firing means to fire the thrust surface whereby the thrust surface strikes the impact block and accelerates the sled carriage for longitudinal movement along the first and second tracks; and (3) observing the effect of the test specimen as the sled is accelerated.

13. A method according to claim 12 for dynamically testing an airbag module, wherein the test buck includes an air bag module mounted therein.

14. A method according to claim 12 for dynamically testing a seat belt system, wherein the test buck includes a seating means for seating the test specimen and seat belt means for securing the test specimen to the seating means.

* * * * *

UNITED STATES PATENT AND TRADEMARK OFFICE
CERTIFICATE OF CORRECTION

PATENT NO. : 5,929,348
DATED : July 27, 1999
INVENTOR(S) : Douglas J. Stein and Frederick M. Peters It is certified that error appears in the above-identified patent and that said Letters Patent is hereby corrected as shown below:

Replace the five sheets of informal drawings with the four sheets of formal drawings attached hereto.

Signed and Sealed this

Fifth Day of February, 2002

*Attest:*

JAMES E. ROGAN
*Director of the United States Patent and Trademark Office*

*Attesting Officer*